United States Patent [19]

Meseguer et al.

[11] Patent Number: 5,037,988

[45] Date of Patent: Aug. 6, 1991

[54] PROCESS FOR PREPARING CEPHALOSPORINS AND INTERMEDIATES THEREFOR

[75] Inventors: José D. Meseguer, Granollers, Asuncion E. Bianchini, Barcelona; Carlos E. L. Padró, Alella; Esteve S. Pitarch, Barcelona, all of Spain

[73] Assignee: Gema S.A., Barcelona, Spain

[21] Appl. No.: 367,656

[22] Filed: Jun. 19, 1989

[30] Foreign Application Priority Data

Jun. 20, 1988 [ES] Spain ................................. 8801910

[51] Int. Cl.$^5$ .......................................... C07D 277/587
[52] U.S. Cl. ................................................... 548/194
[58] Field of Search ........................................ 548/194

[56] References Cited

U.S. PATENT DOCUMENTS 3,786,049  1/1974  Palomo-Coll ..................... 540/316
4,871,860  10/1989  Takaya ............................... 548/194

FOREIGN PATENT DOCUMENTS 403523  5/1975  Spain ................................... 548/194

*Primary Examiner*—Robert Gerstl
*Attorney, Agent, or Firm*—Gerald D. Sharkin; Robert S. Honor; Thomas O. McGovern

[57] ABSTRACT

The invention relates to activated aminothiazolyl-oximinoacetic acid derivatives, their production and their use in the production of e.g. amides, in particular cephalosporin antibiotics.

4 Claims, No Drawings

PROCESS FOR PREPARING CEPHALOSPORINS AND INTERMEDIATES THEREFOR

This invention relates to 2-(2-aminothiazol-4-yl)-2-oxyimino-acetylsulphite-dialkylformimium halide hydrohalides of formula I

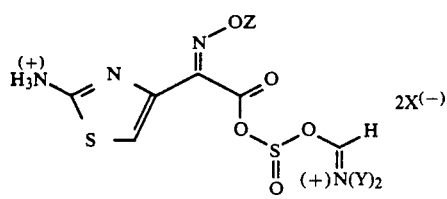

in which
X is halogen
Y is alkyl of 1 to 4 carbon atom and
Z is hydrogen, alkyl, phenalkyl, carbalkoxyalkyl, acyl or carboxyalkyl.

The invention also relates to a process for the production thereof as well as to a process for the use thereof in the production of amides, in particular cephalosporins.

The importance of amides of formula V,

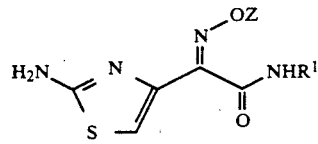

in which
Z is as defined above and
$R_1$ is the structural residue of an amine, usually obtained from amines of formula IV, $$R_1-NH_2 \qquad (IV)$$

in which
$R_1$ is as defined above,
is known. A class of the amides of formula V which is of enormous interest are those produced from amines of formula IV which are 7-aminocephalosporanic acids. Such products are important cephalosporin antibiotics and include cefotaxime:

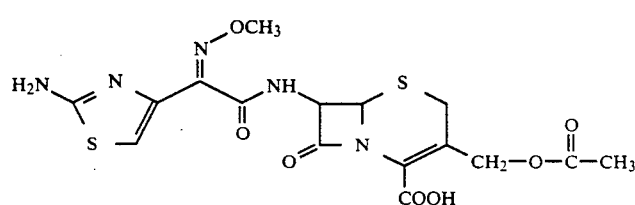

ceftriaxone:

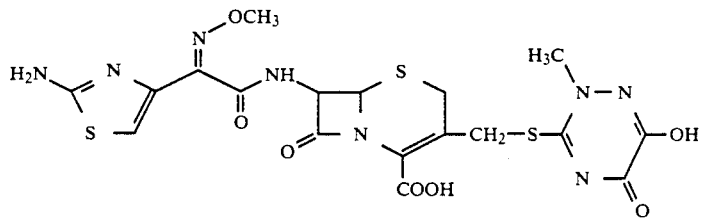

cefmenoxime:

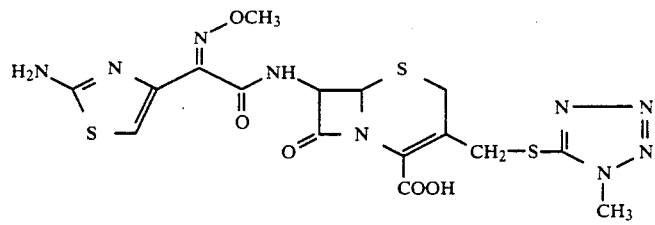

ceftizoxime:

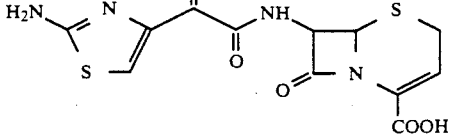

and ceftazidime:

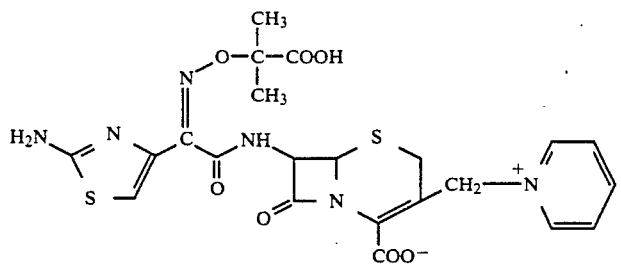

cefetamet, cefuzoname, and desacetylcefotaxime, as well as corresponding monobactam antibiotics in which the amino group is attached to one ring of the β-lactam nucleus.

The preparation of Formula V compounds has been widely described and covered in numerous patents. A large majority of such patents deal with the preparation of compounds having an antibiotic activity.

The possibilities mentioned in the technical literature are, obviously, numerous. Without claiming to be exhaustive, certain cases reported to lead to good results may be cited. For example, the pathway leading to cefotaxime (sodium salt):

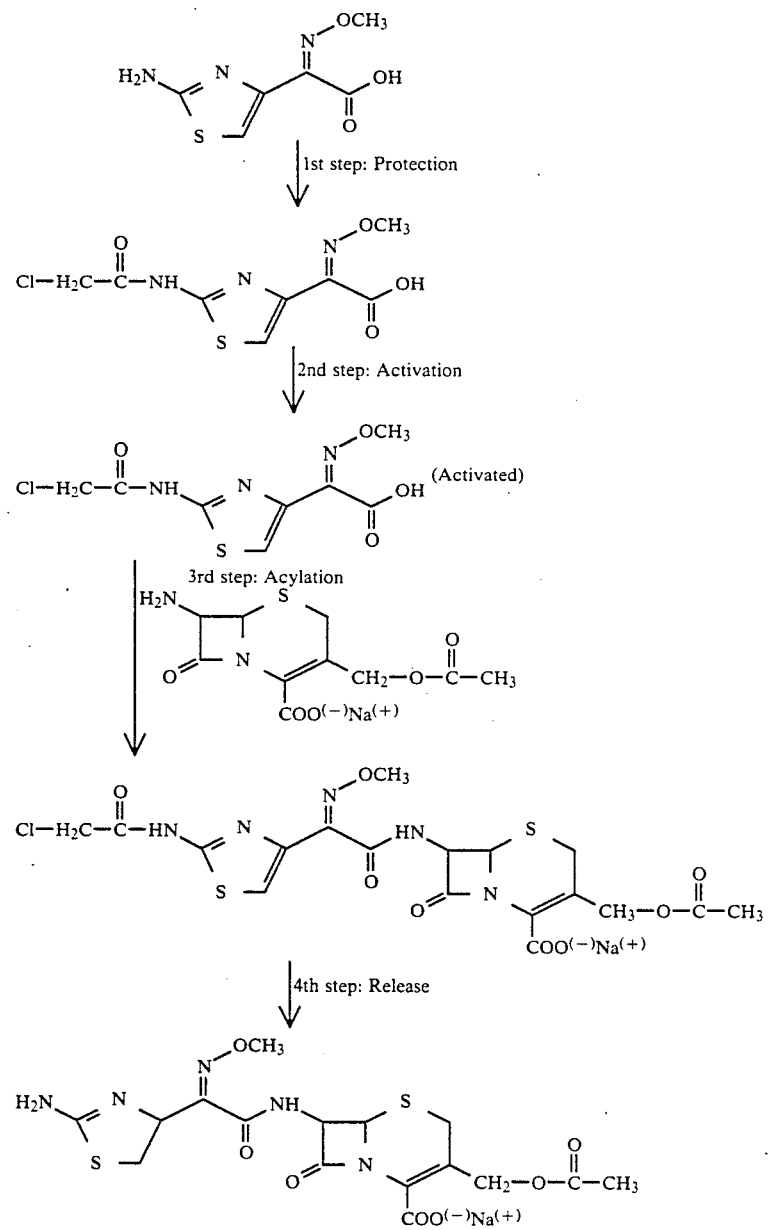

Another known pathway of synthesis is similar to the above, except that the protection of the amino group is effected by triphenylmethylation, instead of by chloroacetylation,

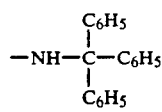

Spanish patents Nos. 457.751 (Takeda), 469.116 and 457.115 (Roussel-Uclaf).

Analytical Profiles (Vol. 11, pp 139–169, Academic Press (1982)) states that the synthesis used for the preparation of cefotaxime is as follows:

with 2-(2-aminothiazol-4-yl)-2-oxyiminoacetic acid of Formula III

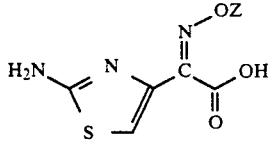

in which
Z is as defined above,
to provide a solution or suspension of the compound of Formula I.

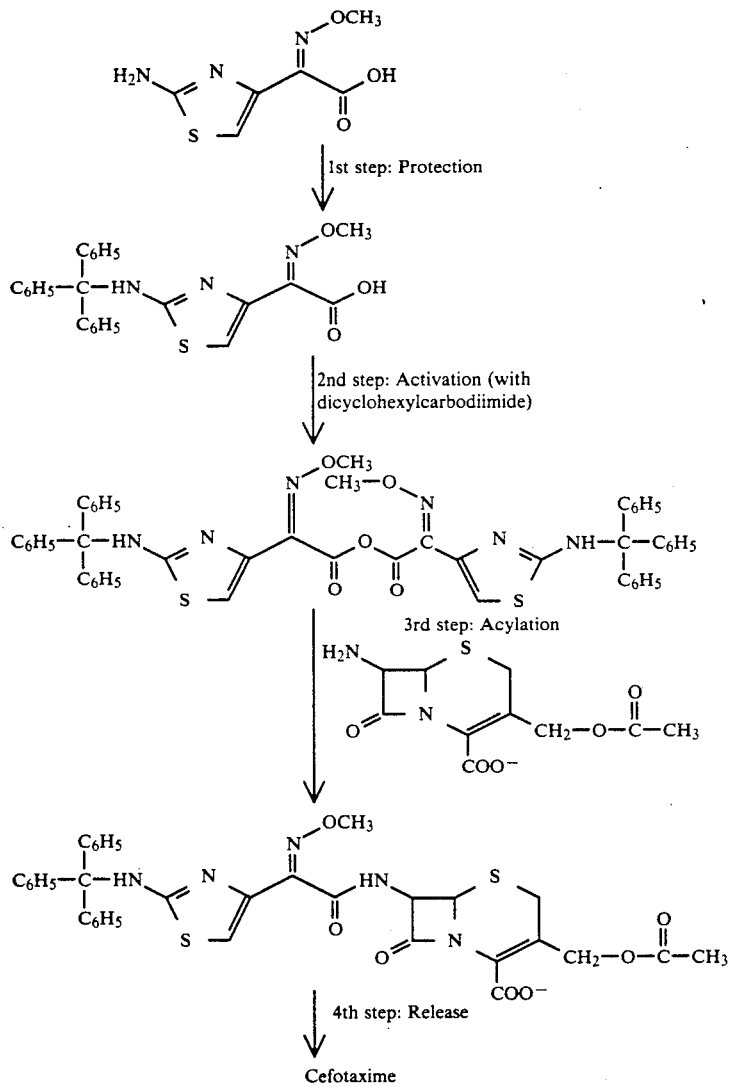

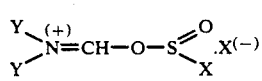

It is an object of the invention to provide a process not subject to the above complexities. In accordance with the invention, compounds of Formula I are produced by a process comprising reacting dialkylforminimum halide halosulfite of Formula II:

$$\underset{Y}{\overset{Y}{\diagdown}}\overset{(+)}{N}=CH-O-\overset{O}{\underset{X}{\overset{\diagup}{S}}}.X^{(-)} \quad (II)$$

in which
X and Y are as defined above

The reaction is preferably conducted at temperatures lying between +5° and −60° C. and it is, furthermore, preferred to use the syn isomer of the 2-(2-aminothiazol-4-yl)-2-oxyimino acetic acid which participates in the reaction.

The use of the compounds of Formula I in the preparation of amides comprises reacting said Formula I compound with an amine of Formula IV $$R_1-NH_2 \quad (IV)$$

where R₁ is as defined above and is preferably selected from the group formed by: $C_1-C_{10}$ alkyl, aryl, arylalkyl, alkenyl, a heterocyclic radical with one to three atoms of nitrogen or nitrogen and sulfur, an arylheterocyclic radical and a system of condensed heterocycles, said reaction preferably being conducted in presence of a hydrogen chloride acceptor, to give a compound of Formula V

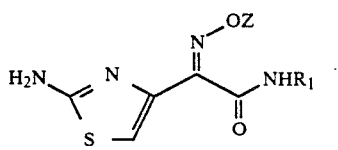
(V)

where R₁ and Z are as hereinbefore defined. The process is of greatest interest when the Formula IV compound is a 7-aminocephalosporanic acid of Formula VI

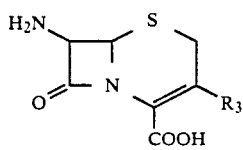
(VI)

where R₃ is selected from the group formed by: —H; —CH₃; —CH₂Cl; —CH₂Br; —CH₂OCOCH₃; —Cl; —CH₂—OCONH₂; a radical of formula —CH₂—S—Q, in which Q is a heterocyclic substituent, such as

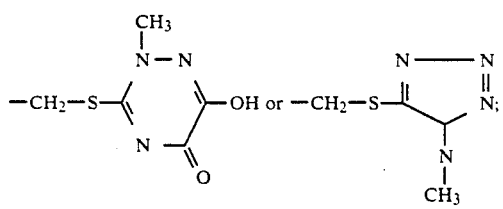

—Cl; —OCH₃; —CH=CH₂; —CH₂OH and —CH₂—R₄, where R₄ is a group which may be introduced by nucleophilic substitution in the acetoxy group of —CH₂—OCOCH₃, or a salt or protected form of said compound of formula VI.

The said hydrogen chloride acceptor is preferably a tertiary nitrogen compound and more particularly a $C_{1-16}$ tertiary or heterocyclic amine, such as a pyridine or quinoline.

The present invention allows the activation of the Formula III acid "in situ" without costly blocking and unblocking operations of the amino group and without the need of intermediate isolations which involve complex purification steps.

The preferred compound of formula II is dimethylformiminium chloridechlorosulfite (D.F.C.S.) described in prior patents to the same applicant (Spanish patents Nos. 361,743, 367,136, 369,916 and 403,523) for activation of the Formula III acid.

The compound of Formula II is easily prepared by reacting approximately equimolar amounts of thionyl chloride and dimethylformamide at room temperature in an appropriate solvent. When the solvent is of the benzene or toluene type, after the mixing stage the Formula II compound separates out and is quickly decanted. Further reference will be made to this fact hereinafter, in view of the importance it confers on the Formula III acid activation step.

Dropwise addition of the Formula II compound to, preferably, a suspension of Formula III acid, suitably in an organic solvent, and at a low temperature leads to the activation thereof in such a way that an amine may be added to prepare the corresponding amide with excellent yield, without the need for subsequent deblocking and costly purification stages.

This synthesis pathway is extraordinarily simple in comparison with those currently being used and represents a notable advance in the preparation of third generation cephalosporin antibiotics.

In fact, compare the normally used pathway:

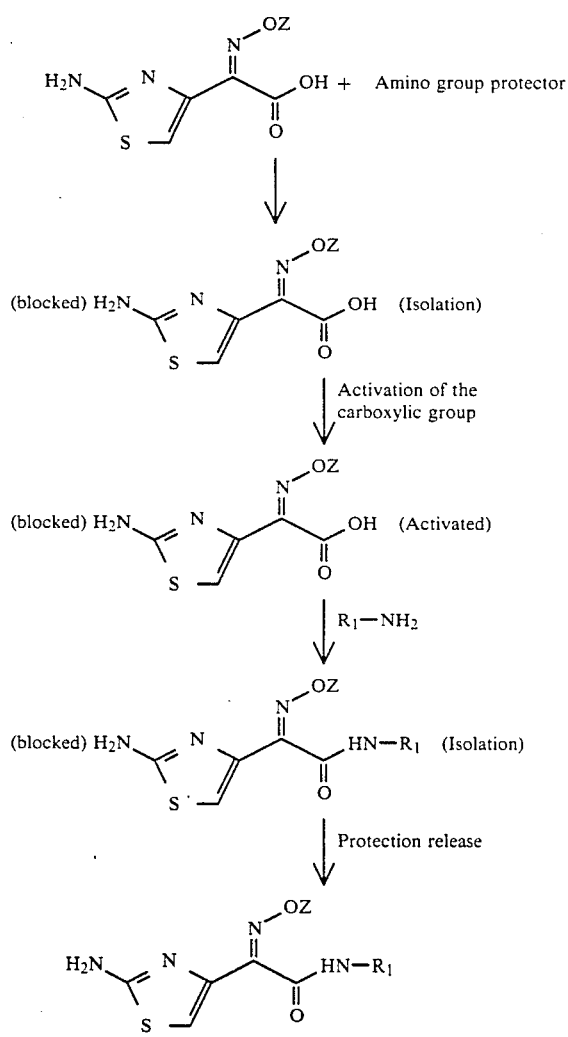

With the pathway of the invention:

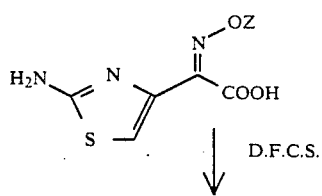

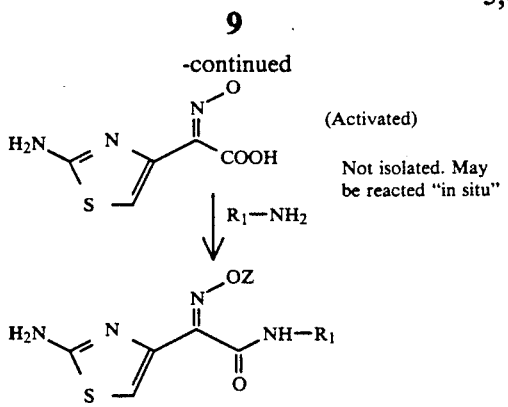

(Activated)
Not isolated. May be reacted "in situ"

In many cases, the process of the invention saves the synthesis, as well as corresponding isolation and purification operations.

The activation of the Formula III acid is conducted via the formation of a mixed, sulfuric carboxylic, anhydride, of Formula I.

One important point is that it is important for the compound of Formula II to conserve the sulfonic residue. In fact, if the Formula II reactant is subjected to rather drastic conditions, the release of $SO_2$ occurs, with formation of a Vilsmeier's reagent as follows:

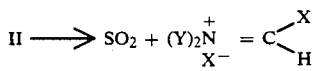

This Vilsmeier's reagent has been used by the authors with very bad results in comparison with those obtained with the Formula II reactant in good agreement with the disclosure of the Fujisawa patent (ES No. 457.191); in Example 13 of this patent the Vilsmeier's reagent is prepared from phosphorus oxychloride and dimethylformamide in the presence of a silylating agent, using large excesses of reactants over the stoichiometrically required amounts. After an extremely complex isolation technique (associated with the lack of selectivity of the reaction), cefotaxime is isolated with a low yield.

Poor results have also been obtained when attempts have been made to form the Formula II reactant in solvents in which it did not separate out in its characteristic form of insoluble oil. Such is the case with methylene chloride and chloroform. The explanation is that the polarity of these solvents does not allow the formation of the Formula II reactant or facilitates its complete or partial conversion to the abovementioned Vilsmeier's reagent.

As a result of problems encountered in producing the Formula V compounds, it has been conventional to use Formula III acid derivatives in which the amino group is blocked. Thus, compounds such as

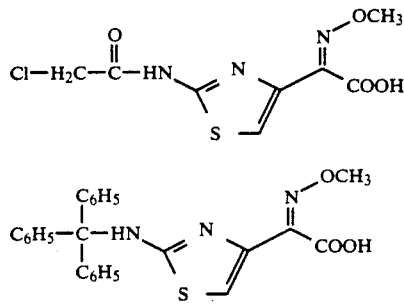

and others are obtainable on the market.

The extremely simple and surprising activation process of the invention has been particularly studied with the preferred "syn" isomeric form of the Formula III acid and with different 7-aminocephalosporanic acids to prepare cephalosporins of great therapeutical interest, such as cefotaxime, cefatriaxone and others mentioned above.

A particularly appropriate form of dissolving the Formula VI compounds for subsequent reaction is to form silyl derivatives using well known techniques. In this manner, the carboxyl group is silylated, e.g. trimethylsilylated, and the amino group of the compound IV may be similarly silylated, partially or completely.

For a satisfactory reaction to be obtained, it is preferred to use a basic compound as acceptor of the hydrogen halide released during the acylation.

Particularly appropriate basic compounds are tertiary amines such as dimethylaniline, pyridine, quinoline, undecylpyridine, triethylamine, tributylamine and others. The Compound II is suitably formed in solvents in which, owing to its apolar nature, it separates out as an insoluble oil in a practically quantitative amount. Toluene has been considered to be particularly appropriate. Once the Formula II reactant has been formed, it is suitably poured dropwise over a suspension or solution of the Formula III acid in an anhydrous medium.

The ideal temperature for activating the Formula III acid lies between $+5°$ and $-60°$ C. Higher temperatures produce reductions in yield in the acylation step, due possibly to total or partial decomposition of the Formula II or I compounds with release of $SO_2$. The same temperature range is appropriate for the acylation step.

The acylation reaction is preferably conducted in an anhydrous medium which may be provided, for example, by an organochlorinated solvent without excluding others used frequently in the chemical and pharmaceutical industry.

The use of conventional silylating agents such as hexamethyldisilazane, bisilylacetamide, bisilylurea, trimethylchlorosilane and others, used alone or in mixture in proportions not precluding the partial or total silylation of the amino group is considered to be appropriate for silylation of Formula VI compounds.

Salts of the Formula VI compound may be employed instead of silylated derivatives, but this is less preferred.

Esters other than silyl esters of the Formula VI compound, such as benzhydryl, trityl, etc. esters may also be used.

Since the Formula V compounds are aminoacids, they may be isolated as such or as pharmaceutically acceptable salts.

To summarize, the best results in the preparation of Formula V compounds are obtained when the Formula I intermediate is formed at low temperature and is thereafter reacted with a 7-aminocephalosporanic acid dissolved in silyl ester form, with the totally or partially silylated amino group in the presence of an acceptor base, without subsequent treatment.

In the compounds of formula I and II, X is preferably chlorine and Y is preferably methyl. In the compounds of formula I, III and V, Z is preferably alkyl, more preferably $C_{1-4}$ alkyl, most preferably methyl. It may alternatively be hydrogen; phenalkyl, preferably phen ($C_{1-4}$) alkyl; carbalkoxyalkyl, e.g. carb ($C_{1-4}$) alkoxy ($C_{1-4}$) alkyl, e.g. —$C(CH_3)_2COOt$-butyl or $CH_2$—

COOt-butyl; acyl, e.g. $C_{2-5}$ alkanoyl; or carboxyalkyl, e.g. carboxymethyl or $-C(CH_3)_2COOH$.

The preferred compounds of formula V are in syn isomeric form and are preferably of formula Va

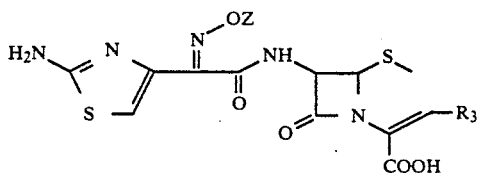

in which Z and $R_3$ are as defined above.

$R_3$ may have any of the significances set forth above but is preferably hydrogen methyl, acetoxy methyl, a radical $-CH_2 S-Q$ (where Q is as defined above) or pyridiniummethyl.

The use of the compounds of formula I of the invention on producing amides of formula V has been described above. The compounds of formula I may also be used for the production of other products such as esters by reaction with suitable alcohols.

There are described hereinafter non-limiting Examples of the invention.

EXAMPLE 1

7((2-2-aminothiazol-4-yl)-2-syn-methoxyiminoacetamido) cephalosporanic acid (Cefotaxime)

A) Activation of the 2-(2-aminothiazol-4-yl)-2-syn-methoxyimino acetic acid (ATMAA)

1.24 ml of dimethylformamide and 1.15 ml of thionyl chloride were added to a compensated pressure funnel containing 6 ml of toluene; the mixture turned turbid almost immediately and an oil separated out, which was decanted in the lower portion (dimethylforminium chloride chlorosulfite-DFCS).

The DFCS was added dropwise over 5 minutes to a suspension of 2.21 g of ATMAA in 13 ml of $CH_2Cl_2$, previously chilled to 0°/5° C., followed by stirring for 30 minutes at 0°/5° C. to give a yellow solution from 2 minutes onwards. This solution, chilled to $-40°/-45°$ C. formed preparation A.

B) 7-aminocephalosporanic acid (7-ACA) solution 13 ml of $CH_2Cl_2$ were mixed with 2.72 g of 7-ACA and 2.1 ml of hexamethyldisilazane, followed by heating to reflux for two hours with energetic stirring. After 50 minutes approximately a solution was obtained. The solution was chilled to 10° C. and 2.0 ml of dimethylaniline were added, followed by cooling to $-50°/-55°$ C. This solution formed preparation B.

C) Acylation

Preparation A was poured over preparation B as quickly as possible, without the temperature rising above $-35°$ C. After 5 minutes stirring, the reaction was considered as terminated, although the acylation time may be extended, without negative influences. Synthesis control by liquid chromatography (HPLC) showed the formation of the title product (Cefotaxime) with a yield lying between 90/95% depending on the potency of the starting product (7-ACA).

Cefotaxime may be isolated from the crude reaction product in acid or salt form.

EXAMPLE 2

7-(2-(2-aminothiazol-4-yl)-2-syn-methoxyiminoacetamido) cephalosporanic acid (Cefotaxime)

Following Example 1, but replacing the dimethylaniline in paragraph B with 5 ml of N,N-methyldodecylaniline, cefotaxime was prepared with a similar yield.

EXAMPLE 3

7-(2-(2-aminothiazol-4-yl)-2-syn-methoxyiminoacetamido)-cephalosporanic acid (Cefotaxime)

Following Example 1, but replacing the dimethylaniline in paragraph B with 1.9 ml of quinoline, cefotaxime was prepared with an 80/85% yield.

EXAMPLE 4

7-(2-(2-aminothiazol-4-yl)-2-syn-methoxyiminoacetamido) cephalosporanic acid (Cefotaxime)

Following Example 1, but replacing the dimethylaniline in paragraph B with 2.23 ml of triethylamine, cefotaxime was prepared with an 80/85% yield.

EXAMPLE 5

7-(2-(2-aminothiazol-4-yl)-2-syn-methoxyiminoacetamido) cephalosporanic acid (Cefotaxime)

Following Example 1, but replacing the dimethylaniline of paragraph B with 1.56 ml of alpha-picoline, cefotaxime was prepared with an 83/88% yield.

EXAMPLE 6

7-(2-(2-aminothiazol-4-yl)-2-syn-methoxyiminoacetamido) cephalosporanic acid (Cefotaxime)

Following Example 1, but replacing the dimethylaniline of paragraph B with 1.29 ml of pyridine, cefotaxime was prepared with a 74/79% yield.

EXAMPLE 7

7-(2-(2-aminothiazol-4-yl)-2-syn-methoxyiminoacetamido) cephalosporanic acid (Cefotaxime)

Following Example 1, but missing out the dimethylaniline of paragraph B and not using any acceptor base.

In this case, the synthesis control by liquid chromatography (HPLC) revealed the formation of approximately 65% of cefotaxime, while approximately 30% of the 7-ACA remains unreacted.

EXAMPLE 8

7(2-2-aminothiazol-4-yl)-2-syn-methoxyiminoacetamido) cephalosporanic acid (Cefotaxime)

A) Activation of the 2-(2-aminothiazol-4-yl)-2-syn-methoxyimino acetic acid (ATMAA)

0.94 ml of dimethylformamide and 0.87 ml of thionyl chloride were added to a compensated pressure funnel containing 6 ml of toluene. The dimethylforminium chloride chlorosulfite (DFCS) was decanted as an insoluble oil from the lower phase.

The DFCS was added dropwise over 15 minutes to a suspension of 2.21 g of ATMAA in 13 ml of $CH_2Cl_2$, previously chilled to 0°/5° C., without obtaining a total solution in this case. The solution was chilled to $-20°/-25°$ C., forming preparation A.

B) 7-aminocephalosporanic acid (7-ACA) solution.

13 ml of $CH_2Cl_2$ were mixed with 2.72 g of 7-ACA and 2.1 ml of hexamethyldisalazane, followed by heating to reflux for two hours with energetic stirring. As from 50 minutes approximately a solution was obtained. The solution was chilled to 10° C. and 2.0 ml of dimethylaniline were added, followed by cooling to −20°/−25° C. This solution formed preparation B.

C) Acylation

Preparation A was poured dropwise over preparation B as quickly as possible, without the temperature rising above −15° C. After 10 minutes stirring at −15°/−20° C., a complete solution was observed. Chromatographic control by HPLC showed a cefotaxime yield of 74/79%.

EXAMPLE 9

7-(2-(2-aminothiazol-4-yl)-2-syn-methoxyiminoacetamido) cephalosporanic acid (Cefotaxime)

Following Example 8, but replacing the 6 ml of toluene of paragraph B with 6 ml of benzene, similar results were obtained.

EXAMPLE 10

7(2-(2-aminothiazol-4-yl)-2-syn-methoxyiminoacetamido) cephalosporanic acid (Cefotaxime)

A) Activation of the 2-(2-aminothiazol-4-yl)-2-syn-methoxyimino acetic acid (ATMAA).

1.24 ml of dimethylformamide and 1.15 ml of thionyl chloride were added to a compensated pressure funnel containing 6 ml of toluene; the mixture turned turbid almost immediately and an oil separated out, which was decanted in the lower portion (DFCS).

The DFCS was added dropwise over 2 minutes to a suspension of 2.21 g of ATMAA in 13 ml of $CH_2Cl_2$, previously chilled to 0°/5° C., followed by stirring for 25 minutes at 0°/5° C., a solution being obtained almost immediately. This solution, chilled to −40°/−45° C. formed preparation A.

B) 7-aminocephalosporanic acid (7-ACA) solution 13 ml of $CH_2Cl_2$ were mixed with 2.72 g of 7-ACA and 3.5 ml of bisilylacetamide and was stirred for two hours. As from 90 minutes a complete solution was obtained. The solution was chilled to 10° C. and 2.0 ml of dimethylaniline were added, followed by cooling to −50°/−55° C. This solution formed preparation B.

C) Acylation

Preparation A was poured over preparation B as quickly as possible, without the temperature rising above −30° C. After 15 minutes, the reaction was considered as terminated.

Liquid chromatography (HPLC) showed the formation of cefotaxime with a yield lying between 88/92%.

EXAMPLE 11

7-(2-(2-aminothiazol-4-yl)-2-syn-methoxyiminoacetamido) cephalosporanic acid (Cefotaxime)

Following Example 10, but replacing the bisilylacetamide of paragraph B with 2.92 g of bisilylurea, cefotaxime was obtained with a similar yield.

EXAMPLE 12

7-(2-(2-aminothiazol-4-yl)-2-syn-methoxyiminoacetamido) cephalosporanic acid (Cefotaxime)

Following Example 1 but refluxing for 15 minutes after stirring for 30 minutes at 0°/5° C. in paragraph A. The cefotaxime yield lies between 35/40%.

EXAMPLE 13

7(2-(2-aminothiazol-4-yl)-2-syn-methoxyiminoacetamido) cefalosporanic acid (Cefotaxime)

Following Example 1 but modifying the temperature for the 30 minutes stirring in paragraph A to 20°/25° C. The cefotaxime yield lies between 75/80%.

EXAMPLE 14

7(2-(2-aminothiazol-4-yl)-2-syn-methoxyiminoacetamido) cephalosporanic acid (Cefotaxime)

A) Activation of the 2-(2-aminothiazol-4-yl)-2-syn-methoxyimino acetic acid (ATMAA)

13 ml of $CH_2Cl_2$ were chilled to 0°/5° C. and 1.24 ml of dimethylformamide and 1.15 ml of thionyl chloride were added, with a complete solution being obtained. The solution was chilled to −5° C. and 2.21 g of ATMAA were added. After 30 minutes an orange coloured solution was obtained.

B) 7-aminocephalosporanic acid (7-ACA) solution 13 ml of $CH_2Cl_2$ were mixed with 2.72 g of 7-ACA and 2.1 ml of hexamethyldisilazane and was heated to reflux for 2 hours with vigorous stirring. As from 50 minutes approximately a solution was obtained. The solution was chilled to 10° C. and 2.0 ml of dimethylaniline were added, followed by cooling to −50°/−55° C. This solution formed preparation B.

C) Acylation

Preparation A was poured over preparation B as quickly as possible, without the temperature rising above −35° C. After 5 minutes stirring, the reaction was considered as terminated, although the acylation time may be extended without negative influences. Control of synthesis by liquid chromatography (HPLC) showed the formation of the title product (Cefotaxime) with a yield lying between 25/30% depending on the potency of the starting product (7-ACA). Note: Following this Example, but deleting the dimethylformamide, i.e. using only thionyl chloride, no formation of cefotaxime is detected by liquid chromatography (HPLC).

EXAMPLE 15

7(2-(2-aminothiazol-4-yl)-2-syn-methoxyiminoacetamido) cephalosporanic acid (Cefotaxime)

A) Activation of the 2-(2-aminothiazol-4-yl)-2-syn-methoxyimino acetic acid (ATMAA)

1.24 ml of dimethylformamide and 1.15 ml of thionyl chloride were added to a compensated pressure funnel containing 6 ml of toluene; the mixture turned turbid almost immediately and an oil separated out, which was decanted in the lower portion (dimethylformiminium chloride chlorosulfite) (DFCS).

The DFCS was added dropwise over 5 minutes to a suspension of 2.21 g of ATMAA in 13 ml of $CH_2Cl_2$, previously chilled to 0°/5° C., followed by stirring for 30 minutes at 0°/5° C. to give a yellow solution from 2 minutes onwards. This solution, chilled to −40°/−45° C. formed preparation A.

B) 7-aminocephalosporanic acid (7-ACA) solution.

2.72 g of 7-ACA were suspended in 14 ml of methylene chloride and the suspension was chilled to 10° C. 1.25 ml of tetramethylguanidine were added, followed by stirring for 15 minutes at 15°/20° C. A yellow-ochre solution was obtained. The solution was chilled to 10° C. and 2.0 ml of dimethylaniline were added, followed by cooling to −25°/−30° C. This solution formed preparation B.

C) Acylation

Preparation A was poured over preparation B as quickly as possible, without the temperature rising above −20° C. After 1 hour stirring at −20°/−25° C., chromatography (HPLC) showed a cefotaxime yield lying between 23/27%.

EXAMPLE 16

7(2-(2-aminothiazol-4-yl)-2-syn-methoxyiminoacetamido) cephalosporanic acid (Cefotaxime)

A) Activation of the 2-(2-aminothiazol-4-yl)-2-syn-methoxyimino acetic acid (ATMAA)

1.24 ml of dimethylformamide and 1.15 ml of thionyl chloride were added to a compensated pressure funnel containing 6 ml of toluene: the mixture turned turbid almost immediately and an oil separated out, which was decanted in the lower portion (DFCS).

The D.F.C.S. was added dropwise over 5 minutes to 13 ml of $CH_2Cl_2$, previously chilled to 0°/5° C. follow by stirring for 15 minutes with a complete solution being obtained at 0°/5° C. 2.21 g of ATMAA were added followed by stirring for 25 minutes at 0°/5° C. An orange coloured solution was obtained.

B) 7-aminocephalosporanic acid (7-ACA) solution 13 ml of $CH_2Cl_2$ were mixed with 2.72 g of 7-ACA and 2.1 ml of hexamethyldisilazane and was heated to reflux for 2 hours with vigorous stirring. As from 50 minutes approximately a solution was obtained. The solution was chilled to 10° C. and 2.0 ml of dimethylaniline were added, followed by cooling to −50°/−55° C. This solution formed preparation B.

C) Acylation

Preparation A was poured over preparation B as quickly as possible, without the temperature rising above −35° C. After 5 minutes stirring, the reaction was considered as terminated, although the acylation time may be extended without negative influences. Control of synthesis by liquid chromatography (HPLC) showed the formation of the title product (Cefotaxime) with a yield lying between 25/30% depending on the potency of the starting product (7-ACA).

EXAMPLE 17

7-(2-(2-aminothiazol-4-yl)-2-syn-methoxyiminoacetamido) cephalosporanic acid (Cefotaxime)

Following Example 1 but amending the acylation step.

C) Acylation

Preparation B was poured over preparation A, over a period of 2 minutes, without the temperature exceeding −35° C.

The formation yield of cefotaxime was between 50/55%.

EXAMPLE 18

7-(2-(2-aminothiazol-4-yl)-2-syn-methoxyiminoacetamido) cephalosporanic acid (Cefotaxime)

Following Example 1 but amending the acylation technique C.

C) Acylation

Preparation A was poured over preparation B as quickly as possible while ensuring that the temperature did not rise above −45° C. After 30 minutes reaction at −40°/45° C., 30 ml of methylene chloride were added, allowing the temperature to rise to −15° C., then 15 ml of water were added and after 5 minutes stirring at 20°/25° C., the lower organic phase was decanted and the process was continued with the aqueous phase, to which 10 ml of acetone was added. The pH was adjusted to 2.1 by addition of NaOH (4N) at 20°/25° C. A solid precipitated out after a few instants; after stirring for 5 minutes, the pH was adjusted to 3.0 and stirring was continued for 60 minutes at 0°/5° C. The product was filtered, washed with 15 ml of aqueous acetone (50%, v/v) to give 4.0 g of cefotaxime (yield 88%).

EXAMPLE 19

7(((2-aminothiazol-4-yl)(methoxyimino)-acetyl)amino)-8-oxo-3(((1,2,5,6-tetrahydro-2-methyl-5,6-dioxo-1,2,4-triazin-3-yl)thio)methyl)-5-thia-1-azabicyclo (4.2.0) oct-2-ene-2-carboxylic acid (Ceftriaxone)

A) Activation of the 2-(2-aminothiazol-4-yl)-2-syn-methoxyimino acetic acid (ATMAA)

1.24 ml of dimethylformamide and 1.15 ml of thionyl chloride were added to a compensated pressure funnel containing 6 ml of toluene; the mixture turned turbid almost immediately and an oil separated out, which was decanted in the lower portion (dimethylformiminium chloride chlorosulfite) (DFCS).

The DFCS was added dropwise over 5 minutes to a suspension of 2.21 g of ATMAA in 13 ml of $CH_2Cl_2$, previously chilled to 0°/5° C., followed by stirring for 30 minutes at 0°/5° C. to give a yellow solution from 2 minutes onwards. This solution, chilled to −40°/−45° C. formed preparation A.

B) 7-amino-3-desacetoxy-3-((2,5-dihydro-6-hydroxy-2-methyl-5-oxo-as-triazin-3-yl)thio)cephalosporanic acid (7-ADTC) solution 15 ml of $CH_2Cl_2$, 3.71 g of 7-ADTC, 4.53 ml of hexamethyldisilazane and 0.07 g of imidazole were mixed together, with heating for two hours, giving a complete solution. The solution was chilled to 10° C. and 2.0 ml of dimethylaniline were added, followed by final cooling to −30°/−35° C. This solution formed preparation B.

C) Acylation

Preparation A was poured over preparation B as quickly as possible, without the temperature rising above −30° C. After 30 minutes stirring at −30°/−25° C., liquid chromatography (HPLC) control showed the formation of the title product (Cefatriaxone) with a yield of 80%.

The cefatriaxone may be isolated from the crude reaction product in acid or salt form.

EXAMPLE 20

7(((2-aminothiazol-4-yl)(methoxyimino)-acetyl)amino)-8-oxo-3(((1,2,5,6-tetrahydro-2-methyl-5,6-dioxo-1,2,4-triazin-3-yl)thio)methyl)-5-thia-1-azabicyclo (4.2.0) oct-2-ene-2-carboxylic acid (Ceftriaxone)

Following Example 19, but modifying the 7-ADTC solution stage (Paragraph B).

50 ml of $CH_2Cl_2$, 8 ml of bisilylacetamide and 3.71 g of 7-ADTC were mixed together; the mixture was stirred for 3 hours at 20°/25° C. to give a complete solution.

The yield in this case was 83%.

EXAMPLE 21

7(((2-aminothiazol-4-yl)(methoxyimino)-acetyl)amino)-8-oxo-3(((1,2,5,6-tetrahydro-2-methyl-5,6-dioxo-1,2,4-triazin-3-yl)thio)methyl)-5-thia-1-azabicyclo (4.2.0) oct-2-ene-2-carboxylic acid (Ceftriaxone)

Following Example 19 but replacing the 2.0 ml of dimethylaniline in paragraph B with 5.0 ml of N,N-methyldodecylaniline.

The yield in this case was 81%.

EXAMPLE 22

7(((2-aminothiazol-4-yl)(methoxyimino)-acetyl)amino)-8-oxo-3(((1,2,5,6-tetrahydro-2-methyl-5,6-dioxo-1,2,4-triazin-3-yl)thio)methyl)-5-thia-1-azabicyclo (4.2.0) oct-2-ene-2-carboxylic acid (Ceftriaxone)

Following Example 19 but carrying out the acylation (paragraph C) at $-15°/-20°$ C.

The yield in this case was 76%.

EXAMPLE 23

The following compounds were prepared with 70% to 96% yields, under similar conditions to those listed in examples 1 to 22, using dimethylformiminium chloride chlorosulfite (DFCS) for the activation of the 2-(2-aminothiazol-4-yl)-2-methoxyimino acetic acid (ATMAA); and reacting the activated form of the ATMAA with an appropriate primary amine of formula $R_1-NH_2$ in methylene chloride at a temperature lying between $-55°/-10°$ C. in the presence of an acceptor base selected from the group formed by dimethylaniline, pyridine, methyldodecylaniline, alpha-picoline, quinoline and triethylamine.

7-(2-(2-aminothiazol-4-yl)-2-syn-methoxyiminoacetamido) desacetoxycephalosporanic acid (CEFETAMET).

7-(((2-aminothiazol-4-yl)(syn-methoxyimino)acetyl)amino-3-(((1-methyl-1H-tetrazol-5-yl)-thio)methyl)-8-oxo-5-thia-1-azabicyclo-(4.2.0) oct-2-ene-2-carboxylic acid (CEFMENOXIME)

7-(((2-aminothiazol-4-yl)(syn-methoxyimino)acetyl)amino-8-oxo-5-thia-1-azabicyclo (4.2.0) oct-ene-2-carboxylic acid (CEFTIZOXIME)

(7 beta-(2-(2-aminothiazol-4-yl)-2-syn-methoxyiminoacetamido-3-((1,2,3-thiadiazol-5-yl)-3-cephem-4-carboxylic acid. (CEFUZONAME).

7-(2-(2-aminothiazol-4-yl)-2-syn-methoxyiminoacetamido) desacetoxycephalosporanic acid (DESACETYLCEFOTAXIME).

We claim:

1. A compound of formula 1,

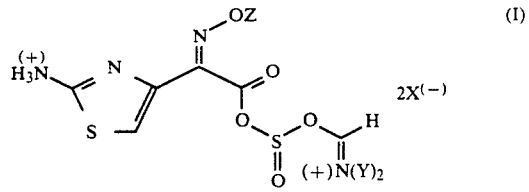

in which
X is halogen
Y is alkyl of 1 to 4 carbon atom and
Z is hydrogen, alkyl, phenalkyl, carbalkoxyalkyl, acyl or carboxyalkyl.

2. 2-(2-aminothiazol-4-yl)-2-methoxyiminoacetyl sulfite dimethylformiminium chloride hydrochloride.

3. A compound of claim 1 or 2 in syn isomeric form.

4. A compound according to claim 1 wherein Z is carboxymethyl or $-C(CH_3)_2COOH$.

* * * * *